US008707472B2

(12) United States Patent
Stachler et al.

(10) Patent No.: US 8,707,472 B2
(45) Date of Patent: Apr. 29, 2014

(54) PROTECTIVE HOOD HAVING A SHIELDED ELASTOMERIC GASKET/SEAL FOR SEALING ENGAGEMENT WITH THE FACE PIECE/MASK OF A SELF-CONTAINED BREATHING APPARATUS OR RESPIRATOR

(75) Inventors: Thomas H. Stachler, Brookville, OH (US); William L. Grilliot, West Milton, OH (US); Michael Schubert, Clayton, OH (US)

(73) Assignee: Honeywell International Inc., Morristown, NJ (US)

( * ) Notice: Subject to any disclaimer, the term of this patent is extended or adjusted under 35 U.S.C. 154(b) by 247 days.

(21) Appl. No.: 12/710,551

(22) Filed: Feb. 23, 2010

(65) Prior Publication Data

US 2010/0287688 A1 Nov. 18, 2010

Related U.S. Application Data

(60) Provisional application No. 61/171,712, filed on Apr. 22, 2009.

(51) Int. Cl.
*A61F 9/02* (2006.01)

(52) U.S. Cl.
USPC .................... 2/428; 2/5; 2/202; 2/205; 2/206; 2/424; 128/201.24; 128/201.25; 128/201.29

(58) Field of Classification Search
USPC .......... 2/424, 5, 173, 205, 428, 410, 202, 6.3, 2/6.7, DIG. 3, 2.11, 2.14, 2.15, 901, 457, 2/458, 7, 8, 84, 203, 275; 128/201.23, 128/201.29, 206.24; 112/402, 475.21, 112/475.06, 475.11, 441, 141, 147, 153; 156/93
See application file for complete search history.

(56) References Cited

U.S. PATENT DOCUMENTS

| | | | | |
|---|---|---|---|---|
| 3,090,047 | A * | 5/1963 | De Grazia | 112/425 |
| 5,806,097 | A * | 9/1998 | Grilliot et al. | 2/81 |
| 6,006,360 | A * | 12/1999 | Reed | 2/202 |
| 6,478,025 | B1 * | 11/2002 | Yort et al. | 128/201.25 |
| 6,691,314 | B1 * | 2/2004 | Grilliot et al. | 2/5 |
| 6,763,835 | B1 * | 7/2004 | Grove et al. | 128/857 |
| 6,775,850 | B1 * | 8/2004 | Grilliot et al. | 2/424 |
| 2002/0046752 | A1 * | 4/2002 | Tischer et al. | 128/201.29 |
| 2003/0110553 | A1 * | 6/2003 | Aldridge | 2/458 |
| 2006/0021118 | A1 * | 2/2006 | Culler et al. | 2/457 |
| 2006/0102177 | A1 * | 5/2006 | Lewis et al. | 128/201.23 |
| 2007/0169247 | A1 * | 7/2007 | Mordecai et al. | 2/81 |
| 2008/0115261 | A1 * | 5/2008 | Grilliot et al. | 2/458 |

* cited by examiner

*Primary Examiner* — Khoa Huynh
*Assistant Examiner* — Khaled Annis
(74) *Attorney, Agent, or Firm* — Wood, Phillips, Katz, Clark & Mortimer

(57) ABSTRACT

A protective hood (18) of a protective garment (16) is provided for use with a face piece or mask (12) worn by a user. The hood (18) includes an outer shell (30) having a peripheral edge (20), and a gasket (22) that extends from the peripheral edge (20) to an interior of the hood (18) for sealing engagement with the face piece or mask (12) with the gasket (22) being covered by the outer shell (30) of the hood (18) when worn by a user.

16 Claims, 5 Drawing Sheets

PROTECTIVE HOOD HAVING A SHIELDED ELASTOMERIC GASKET/SEAL FOR SEALING ENGAGEMENT WITH THE FACE PIECE/MASK OF A SELF-CONTAINED BREATHING APPARATUS OR RESPIRATOR

CROSS-REFERENCE TO RELATED APPLICATIONS

This application claims the benefit of the filing date of U.S. Provisional Application No. 61/171,712, filed Apr. 22, 2009, which is hereby incorporated by reference.

FEDERALLY SPONSORED RESEARCH OR DEVELOPMENT

This invention was made with Government support under Contract No. W91CRB-04-C-027 awarded by the United States Department of the Army. The Government has certain rights in the invention.

MICROFICHE/COPYRIGHT REFERENCE

Not Applicable.

FIELD OF THE INVENTION

This invention relates to protective garments wearable by a firefighter or other emergency worker or first responder, and particularly protective garments utilized with a face piece or mask and including a protective hood.

BACKGROUND OF THE INVENTION

Commonly when called upon to deal with hazardous chemical or biological materials, a firefighter, emergency worker or other emergency responder wears a protective garment, such as protective coveralls or bunker gear, having a hood, and a face piece or mask, which is connected to a self-contained breathing apparatus (SCBA) or to a respirator having an air filter. In some conventional constructions, it is known to provide an elastomeric gasket/seal extending forwardly from the peripheral edge of the hood to engage an exterior surface of the face/conformable gasket. One example of such a construction is shown in U.S. Pat. No. 4,174,710 issued Nov. 20, 1979. While such constructions may be suitable for their intended purpose, there is always room for improvement

SUMMARY OF THE INVENTION

In accordance with one feature of the invention, the hood of a protective garment includes a gasket/seal that extends to an interior of the hood from a peripheral edge or hem of the hood for sealing engagement with a face piece or mask worn by a firefighter, emergency worker or other emergency responder, such that the gasket/seal is covered by the material forming the hood when worn by a user.

According to one feature of the invention, a protective hood of a protective garment is provided for use with a face piece or mask worn by a user. The hood includes an outer shell having a peripheral edge, and a gasket that extends from the peripheral edge to an interior of the hood for sealing engagement with the face piece or mask with the gasket being covered by the outer shell of the hood when worn by a user.

As one feature, the peripheral edge is defined by a hem formed in the outer shell, and the gasket is fixed to the hem.

In one feature, the hood is a multilayer construction and includes a moisture/vapor/chemical barrier liner. According to a further feature, the peripheral edge is defined by a hem formed in the outer shell, and the gasket is fixed to the hem. In a further feature, a portion of the outer shell is folded over a peripheral edge of the barrier liner to define the hem.

According to one feature, the gasket is connected to the hem by a line of stitching.

As one feature, the hood is a multilayer construction and includes an inner liner, and moisture/vapor/chemical barrier liner between the inner liner and the outer shell. In a further feature, the inner liner is a thermal barrier. In one feature, the peripheral edge is defined by a hem formed in the outer shell, and the gasket is fixed to the hem. According to a further feature, a portion of the outer shell is folded over a peripheral edge of the barrier liner to define the hem, and a folded peripheral edge of the inner liner is sandwiched between the gasket and the outer shell. As a further feature, the outer shell, the barrier liner and the inner liner are connected to each other at the hem by a first line of stitching that passes through a single layer of each of the outer shell, the barrier liner, and the inner liner. In yet a further feature, the gasket is attached to the hem by a second line of stitching that passes through the outer shell, the barrier liner and the inner liner. According to a yet a further feature, the second line of stitching passes through two layers of the outer shell and two layers of the inner liner.

In one feature, the gasket has a flange portion that underlies the hem and an angled portion that extends at an angle to the flange portion so as to better conform to the face piece when worn by a user. As a further feature, the gasket is a strip of elastomeric material that had been molded or extruded.

According to one feature, the hood has a zippered opening and a length of the gasket extends past one side of the zippered opening so at to be overlaid by a portion of the gasket on an opposite side of the zippered opening with the zippered opening in a closed position.

Other objects, features, and advantages of the invention will become apparent from a review of the entire specification, including the appended claims and drawings.

DETAILED DESCRIPTION OF THE PREFERRED EMBODIMENT

Figure 1:
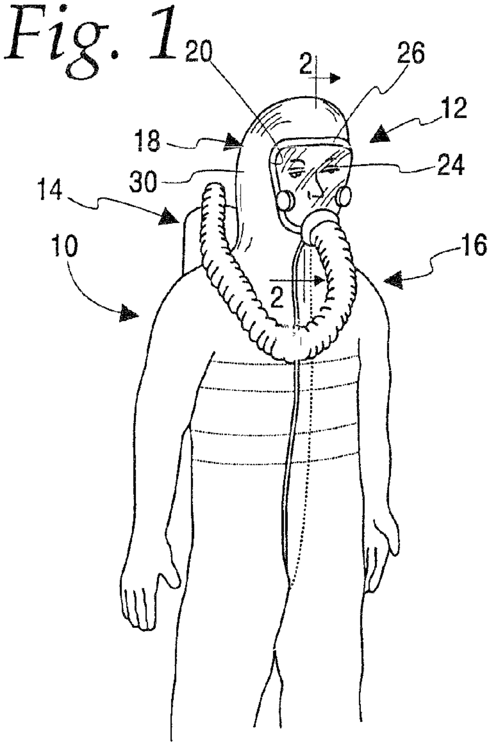
FIG. 1 is a perspective view of a person, such as a firefighter or other emergency worker or first responder, wearing a protective combination comprising a face piece/mask and a protective garment including a protective hood with an elastomeric gasket embodying the invention.

A protective combination 10 worn by a firefighter or other emergency worker or first responder is shown in FIG. 1 and includes a face piece or mask 12 suitable for a use with a respirator or self-contained breathing apparatus (SCBA) 14, and a protective garment 16 including an integrated protective hood 18. It is highly preferred that the protective combination 10 conform to National Fire Protection Association (NFPA) Standard 1971, 2007 Edition (or the most recent edition), the disclosure of which is incorporated herein by reference. The protective combination 10 may also conform to one or more other National Fire Protection Association (NFPA) standards, for example as exemplified in any editions of NFPA 1976; NFPA 1951 USAR; NFPA 1977; NFPA 1999 EMS; and/or NFPA 1991, 1992, 1994 HAZMAT; the disclosures of which are incorporated herein by reference. As will be described in more detail below, the hood 18 has a peripheral edge 20 that defines an opening surrounding a periphery of the face mask 12. The hood 18 includes an elastomeric gasket or seal 22 (best seen in FIG. 2) that extends from the peripheral edge 20 towards an interior of the hood 18 for sealing engagement with the face piece/mask 12, with the gasket 22 and the periphery of the face piece/mask 20 being covered by the material forming the hood 18.

Figure 2:
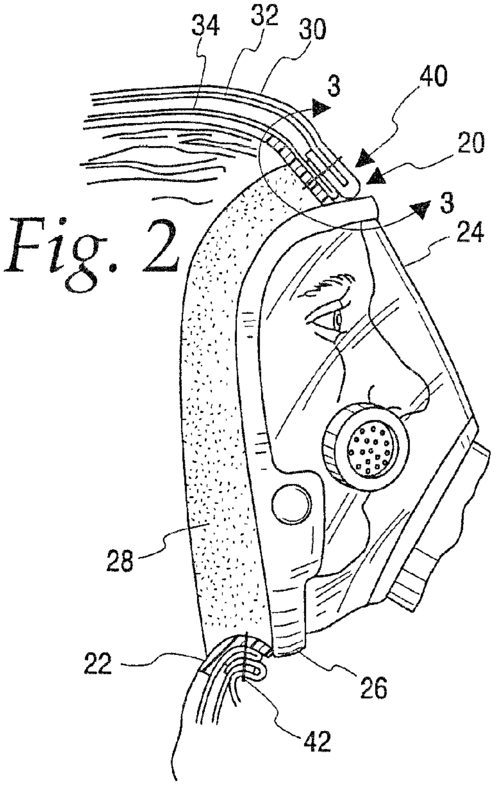
FIG. 2 is a fragmentary, enlarged sectional view taken along line 2-2 in FIG. 1.

As best seen in FIG. 2, the face piece/mask 12 includes a transparent window 24 surrounded by a frame 26, with an elastomeric, face-conformable gasket 28 extending from the frame 26 for sealing engagement with the face of a wearer. There are many suitable types of such face piece/masks 12 known in the art, the further details of which are outside the scope of the invention and can readably be supplied by a person having ordinary skill in the art.

As best seen in Fig, 2, the hood 18 is preferably a multi-layered construction and includes an outer shell 30, an inner moisture/vapor/ chemical barrier liner 32, and, preferably, an inner liner 34 of a material suitable to protect the moisture/vapor/chemical barrier 32 from contact and/or abrasive wear from the user's body and/or other hardware worn on the user's head, (such as for example, harness or straps for the face piece/mask 12), and/or to act as a thermal barrier/liner, The outer shell 30 can be made from any suitable fire resistant, thermal resistant and/or wear resistant (i.e., resistant to cuts, snaps, tears, and abrasions) material, some examples of which include Kevlar®, Nomex®,Basofil, PBI (polybenzimidazole), and PBO (poly(p-phenylene-benzobisoxazole)) materials. The moisture/vapor/chemical barrier 32 can be made of any suitable material that is highly resistant to the passage of moisture, vapor and chemicals. One example of a suitable material for the barrier 32 is supplied by W. L. Gore & Associates, Inc. under the CHEMPAK® trademark. One preferred suitable material for the liner 34 is a Kevlar® mesh material. Preferably, the remainder of the protective garment 16 also includes an outer shell and an inner moisture/vapor/ chemical barrier liner made of suitable materials, preferably the same materials as those used in the hood 18. The peripheral edge 20 of the hood 18 is defined by a hem 40, and the gasket 22 is fixed to the hem 40 by any suitable means, which in the illustrated embodiment is a line of stitching 42 that non-detachably attaches to gasket 22 to the hood 18. The gasket 22 extends totirards the interior of the hood 18 so that the gasket 22 is overlaid by the outer shell 30 and moisture/vapor/chemical barrier 32 of the hood 18 when worn by a user. The gasket 22 can be made of any suitable elastomeric material, such as, for example, suitable rubber, such as a butyl rubber.

It should be noted that the liner 34 is not included in the embodiments of the hood 18 shown in FIGS. 5-8.

Figure 3:
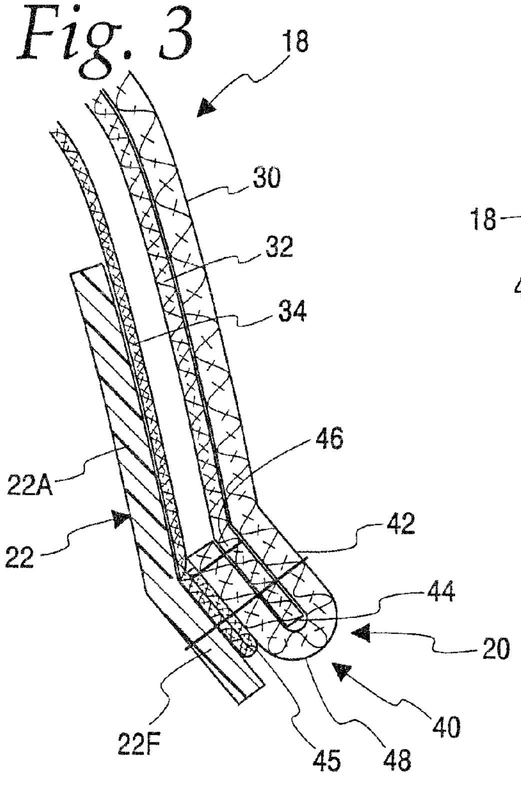
FIG. 3 is an enlarged view of a portion of the hood encircled by line 3-3 in FIG. 2.

With reference to FIG. 3, one preferred form for the construction details of the hem 40 can be seen. In this construction, the outer shell 30 is folded over a peripheral edge 44 of the barrier 32, and a folded peripheral edge 45 of the inner liner 34 is sandwiched between the folded outer shell 30 and the gasket 22. Preferably, in forming this construction, the barrier 32, outer shell 30, and liner 34 are first connected by a line of stitching 46 that passes through a single layer of each of the barrier 32, outer shell 30, and liner 34, with the liner 34 then being folded inward upon itself and the peripheral hem 40 being formed by connecting the gasket 22 to the hem construction with the line of stitching 42. As one alternate construction, the liner 34 can also be sandwiched within the fold 48 of the outer shell 30 between the material of the outer shell 30 and the barrier 32 so that the gasket 22 is attached directly to the fold 48 of the outer shell 30.

The gasket 22 can be formed using any suitable technique, including, for example, molding or extrusion. Furthermore, the gasket 22 can be provided in the form of a strip that is attached continuously around the peripheral edge 20/hem 40 of the hood 18. Furthermore, as best seen in FIG. 3, in one preferred form, the gasket 22 has a flange portion 22F that has approximately the same width as the hem 40, and an angled portion 22A that extends at an angle from the flange portion 22F (approximately 30° in the illustrated embodiment) in its as molded/extruded shape so as to better conform to the gasket/seal 28 of the face piece/mask 12 when worn by a user.

Figure 4:
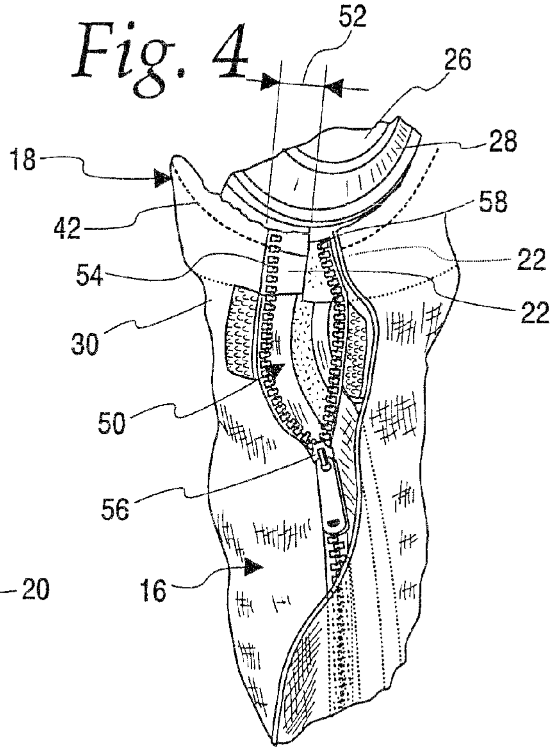
FIG. 4 is a fragmentary, enlarged perspective view from the front showing an embodiment of the garment and hood having a zippered opening.
Figure 5:
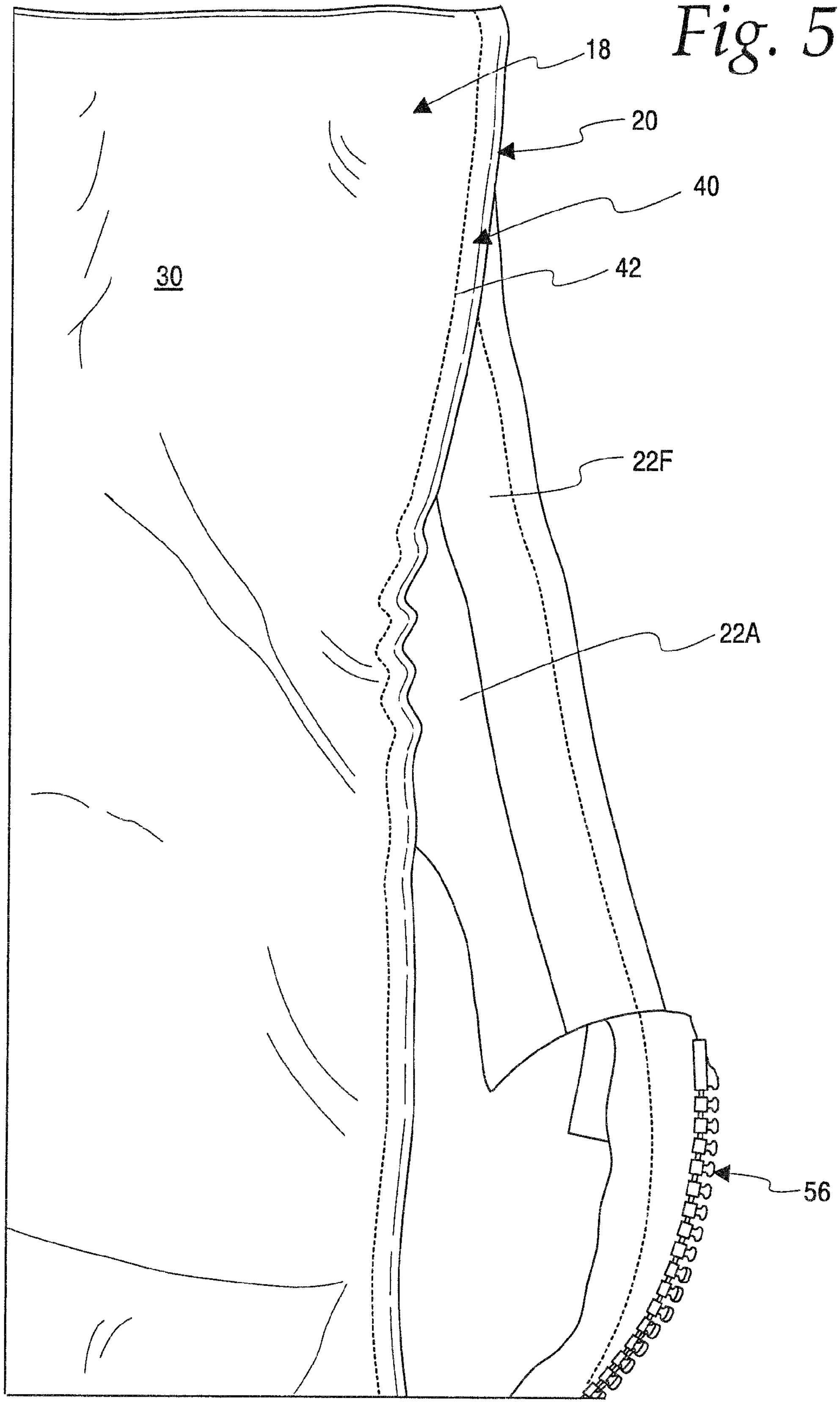
FIGS. 5 and 6 are perspective views showing one embodiment of the garment and hood together with the gasket.
Figure 6:
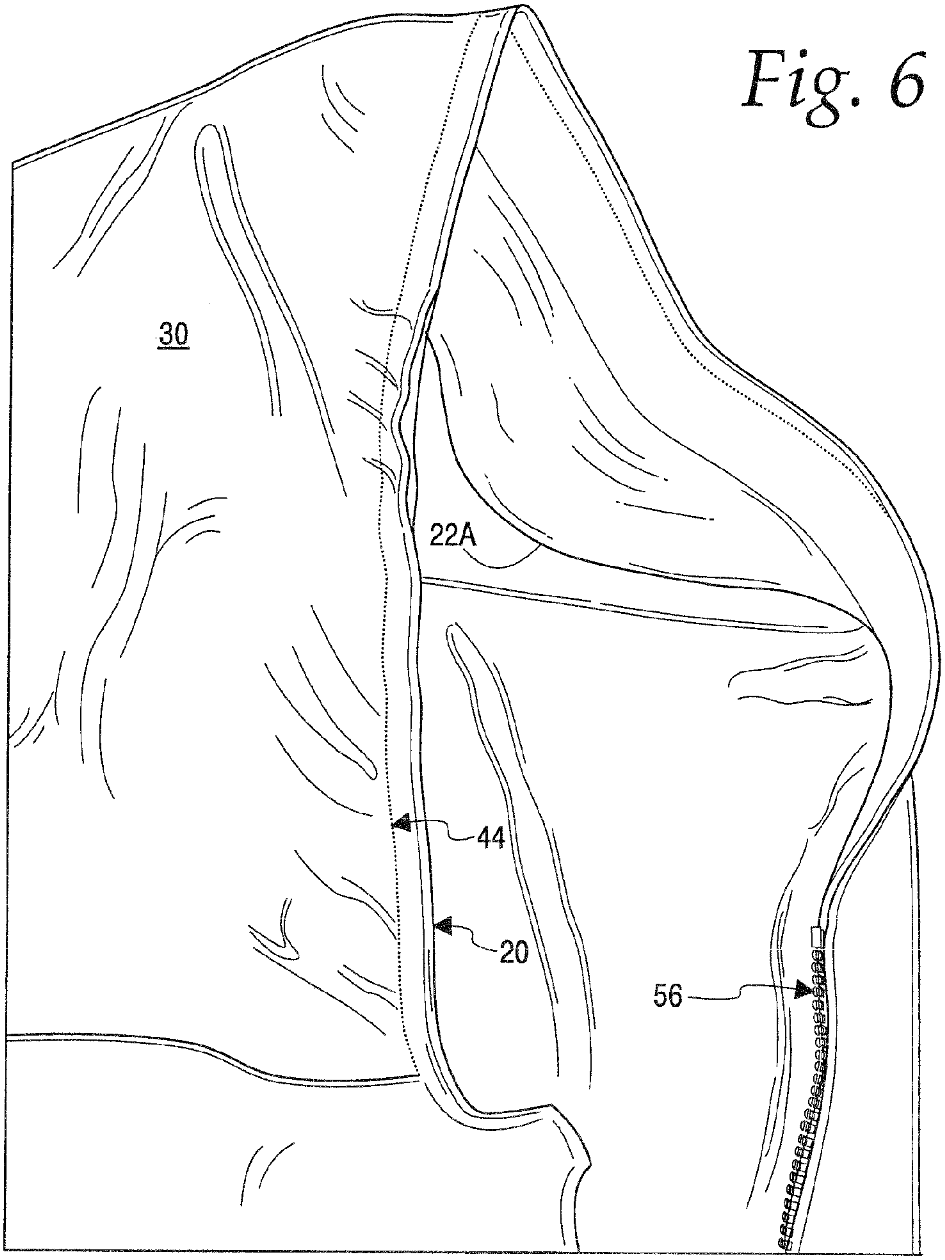
Figure 7:
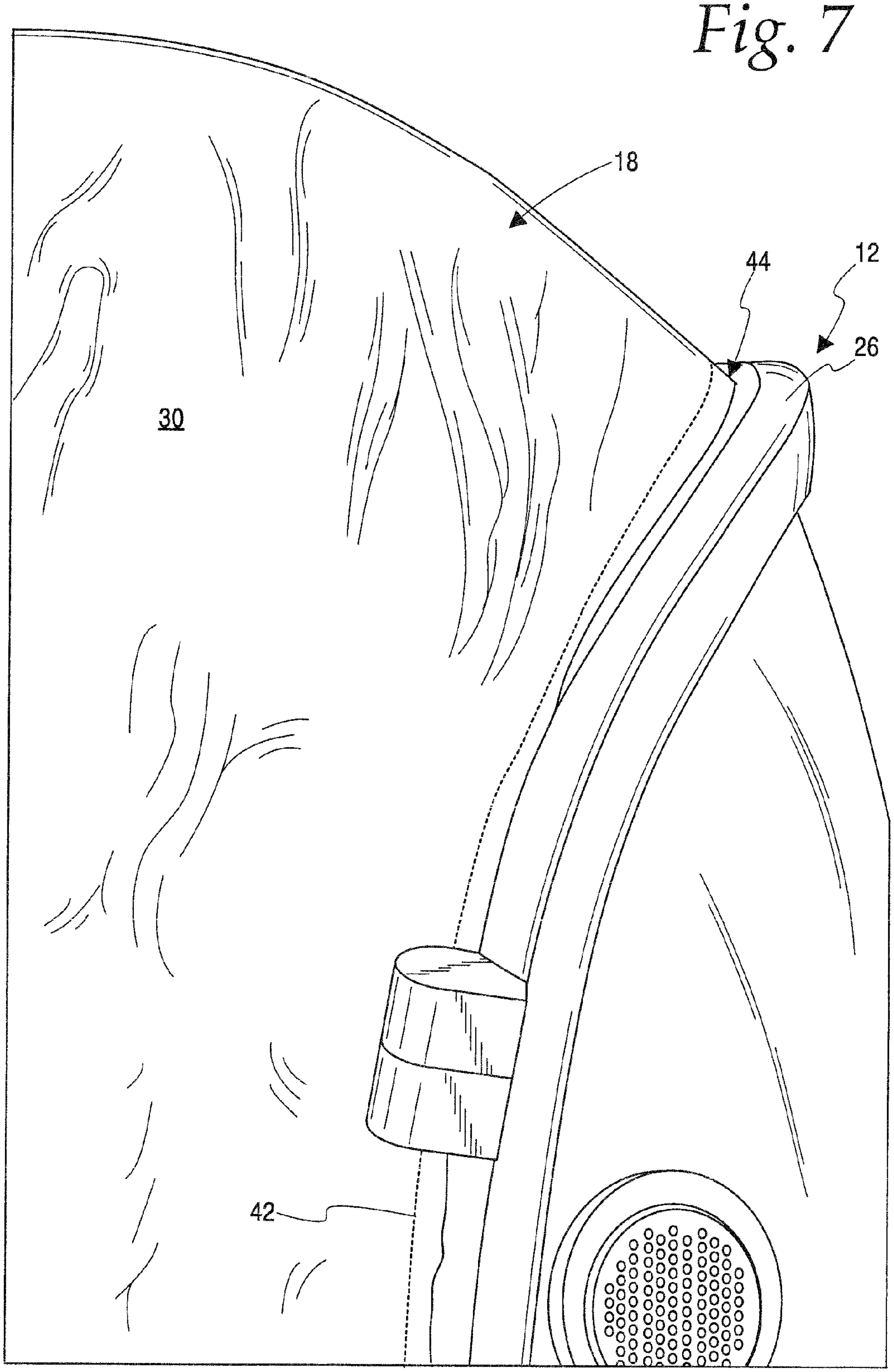
FIGS. 7 and 8 are perspective views showing the hood of FIGS. 5 and 6 in connection with a face piece/mask, with FIG. 8 showing a portion of the peripheral edge of the hood being pulled away from the face piece/mask.
Figure 8:
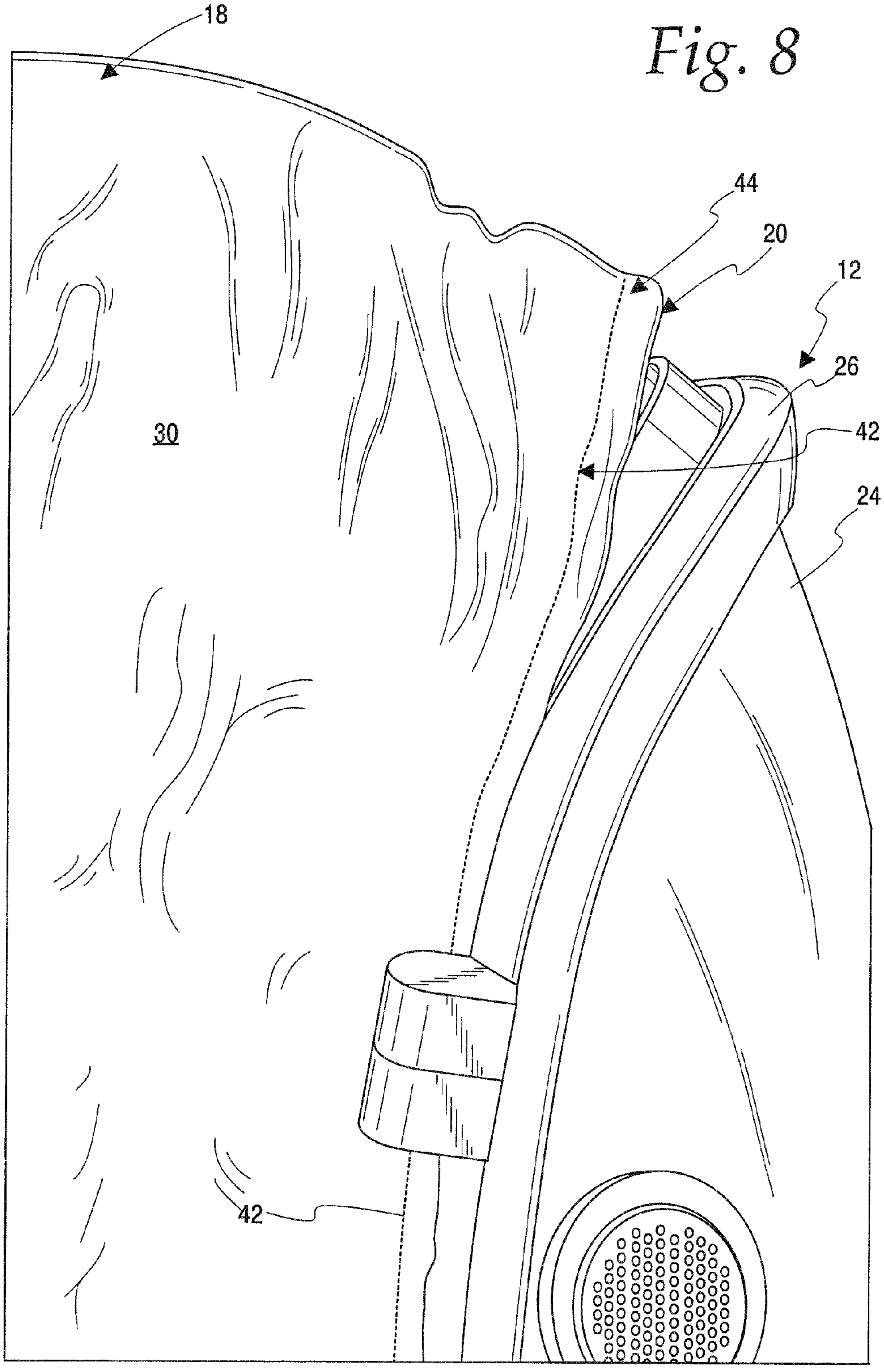

As best seen in FIG. 4, in constructions wherein the garment 16 and hood 18 have a zippered opening 50, the gasket 22 can be provided such that a length 52 of the gasket 22 extends past one side 54 of the zippered opening 50 so as to be overlaid by the zipper 56 and the portion of the gasket 22 on the opposite side 58 of the opening 50 when the zipper 56 is closed. Alternatively, the gasket 22 can be provided such that it terminates immediately adjacent each side of the zippered opening 50 so as to abut when the zipper 56 is closed.

It should be appreciated that by attaching the gasket 22 so that it extends to the interior of the hood 18, as opposed outwardly to an exterior of the hood 18, the material of the hood 18 shields the gasket 22 from heat exposure in use. Furthermore, attaching the gasket 22 at the hem 40 of the assembled hood 18 eliminates the need for sealing the stitching 42 to prevent leakage.

As can be seen in FIGS. 5-8, the face piece/mask 12 is designed to be operatively worn by a user in a state fully separated from the outer shell 30. The outer shell 30 is designed to be operatively worn by being changed from a state fully separated from the face piece or mask that is operatively worn by a user and moved relative to the operatively worn face piece or mask so as to thereby cause the gasket to reside between the outer shell and face piece or mask and make sealing engagement with the face piece or mask.

The invention claimed is:

1. In combination:

a) a protective hood for a protective garment, the hood comprising:

an outer shell having a peripheral edge; and a gasket that extends from the peripheral edge to an interior of the hood, the gasket being permanently attached to the hood; and b) a face piece or mask, the face piece or mask designed to be operatively worn by a user in a state fully separated from the outer shell, the outer shell designed to be operatively worn by being changed from a state fully separated from the face piece or mask that is operatively worn by a user and moved relative to the operatively worn face piece or mask so as to thereby cause the gasket to reside between the outer shell and face piece or mask and make sealing engagement with the face piece or mask.

2. The combination of claim 1 wherein the peripheral edge is defined by a hem formed in the outer shell, and the gasket is fixed to the hem.

3. The combination of claim 1 wherein the hood is a multilayer construction and includes a moisture/vapor/chemical barrier liner that is resistant to the passage of moisture, vapor and chemicals.

4. The combination of claim 3 wherein the peripheral edge is defined by a hem formed in the outer shell, and the gasket is fixed to the hem.

5. The combination of claim 4 wherein a portion of the outer shell is folded over a peripheral edge of the barrier liner to define the hem.

6. The combination of claim 1 wherein the hood is a multilayer construction and includes an inner liner, and moisture/vapor/chemical barrier liner between the inner liner and the outer shell liner that is resistant to the passage of moisture, vapor and chemicals.

7. The combination of claim 6 wherein the inner liner is a thermal barrier.

8. The combination of claim 6 wherein the peripheral edge is defined by a hem formed in the outer shell, and the gasket is fixed to the hem.

9. The combination of claim 1 wherein the hood has a zippered opening and a length of the gasket extends past one side of the zippered opening so as to be overlaid by a portion of the gasket on an opposite side of the zippered opening with the zippered opening in a closed position.

10. In combination:

a) a protective hood for a protective garment, the hood comprising:

an outer shell having a peripheral edge;

a gasket that extends from the peripheral edge to an interior of the hood; and b) a face piece or mask, the face piece or mask designed to be operatively worn by a user in a state fully separated from the outer shell, the outer shell designed to be operatively worn by being changed from a state fully separated from the face piece or mask that is operatively worn by a user and moved relative to the operatively worn face piece or mask so as to thereby cause the gasket to reside between the outer shell and face piece or mask and make sealing engagement with the face piece or mask, wherein a portion of the outer shell is folded over a peripheral edge of the barrier liner to define the hem; and wherein the gasket is connected to the hem by a line of stitching.

11. A protective hood of a protective garment for use with a face piece or mask worn by a user, the hood comprising:

an outer shell having a peripheral edge;

a gasket that extends from the peripheral edge to an interior of the hood for sealing engagement with the face piece or mask with the gasket being covered by the outer shell of the hood when worn by a user, the gasket being nondetachably attached to the hood;

wherein the hood is a multilayer construction and includes an inner liner, and moisture/vapor/chemical barrier liner between the inner liner and the outer shell;

wherein the peripheral edge is defined by a hem formed in the outer shell, and the gasket is fixed to the hem; and wherein a portion of the outer shell is folded over a peripheral edge of the barrier liner to define the hem, and a folded peripheral edge of the inner liner is sandwiched between the gasket and the outer shell.

12. The hood of claim 11 wherein the outer shell, the barrier liner and the inner liner are connected to each other at the hem by a first line of stitching that passes through a single layer of each of the outer shell, the barrier liner, and the inner liner.

13. The hood of claim 12 wherein the gasket is attached to the hem by a second line of stitching that passes through the outer shell, the barrier liner and the inner liner.

14. The hood of claim 13 wherein the second line of stitching passes through two layers of the outer shell and two layers of the inner liner.

15. In combination:

a) a protective hood for a protective garment, the hood comprising:

an outer shell having a peripheral edge;

a gasket that extends from the peripheral edge to an interior of the hood; and b) a face piece or mask, the face piece or mask designed to be operatively worn by a user in a state fully separated from the outer shell, the outer shell designed to be operatively worn by being changed from a state fully separated from the face piece or mask that is operatively worn by a user and moved relative to the operatively worn face piece or mask so as to thereby cause the gasket to reside between the outer shell and face piece or mask and make sealing engagement with the face piece or mask, wherein the peripheral edge is defined by a hem formed in the outer shell, and the gasket is fixed to the hem, wherein the gasket has a flange portion that underlies the hem and an angled portion that extends at an angle to the flange portion inwardly from the peripheral edge toward the interior of the hood so as to conform to the face piece when worn by a user.

16. The combination of claim 15 wherein the gasket is a strip of elastomeric material that had been molded or extruded.

* * * * *